(12) United States Patent
Heyman et al.

(10) Patent No.: US 6,371,960 B2
(45) Date of Patent: Apr. 16, 2002

(54) DEVICE FOR INSERTING A FLEXIBLE INTRAOCULAR LENS

(75) Inventors: Thomas M. Heyman, Chino Hills; Lauren L. Kanner, Santa Ana; Bradley S. Stone, Irvine, all of CA (US)

(73) Assignee: Bausch & Lomb Surgical, Inc., Rochester, NY (US)

( * ) Notice: Subject to any disclaimer, the term of this patent is extended or adjusted under 35 U.S.C. 154(b) by 0 days.

(21) Appl. No.: 09/081,130

(22) Filed: May 19, 1998

(51) Int. Cl.$^7$ .............................................. A61F 9/007
(52) U.S. Cl. ..................................................... 606/107
(58) Field of Search .......................... 606/107; 623/6.12

(56) References Cited

U.S. PATENT DOCUMENTS

| | | |
|---|---|---|
| 3,991,426 A | 11/1976 | Flom et al. |
| 4,053,953 A | 10/1977 | Flom et al. |
| 4,214,585 A | 7/1980 | Bailey, Jr. |
| 4,244,370 A | 1/1981 | Furlow et al. |
| 4,573,998 A | 3/1986 | Mazzocco |
| 4,600,003 A | 7/1986 | Lopez |
| 4,600,004 A | 7/1986 | Lopez et al. |
| 4,619,256 A | 10/1986 | Horn |
| 4,634,423 A | 1/1987 | Bailey, Jr. ..................... 604/51 |
| 4,681,102 A | 7/1987 | Bartell |
| 4,699,140 A | 10/1987 | Holmes et al. |
| 4,702,244 A | 10/1987 | Mazzocco |
| 4,715,373 A | 12/1987 | Mazzocco et al. |
| 4,731,079 A | 3/1988 | Stoy |
| 4,747,404 A | 5/1988 | Jampel et al. |
| 4,750,498 A | 6/1988 | Graham |
| 4,763,650 A | 8/1988 | Hauser |
| 4,765,329 A | 8/1988 | Cumming et al. |
| 4,822,360 A | 4/1989 | Deacon |
| 4,834,094 A | 5/1989 | Patton et al. |
| 4,836,201 A | 6/1989 | Patton et al. |
| 4,836,202 A | 6/1989 | Krasner |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,950,289 A | 8/1990 | Krasner |
| 4,955,889 A | 9/1990 | Van Gent |
| 4,957,505 A | 9/1990 | McDonald |
| 4,976,716 A | 12/1990 | Cumming |
| 4,993,936 A | 2/1991 | Siepser |
| 5,007,913 A | 4/1991 | Dulebohn et al. |
| 5,066,297 A | 11/1991 | Cumming .................... 606/107 |
| 5,098,439 A | 3/1992 | Hill et al. |
| 5,123,905 A | 6/1992 | Kelman |
| 5,190,552 A | 3/1993 | Kelman |
| 5,242,450 A | 9/1993 | McDonald |
| 5,275,604 A | 1/1994 | Rheinish et al. |
| 5,292,324 A | 3/1994 | McDonald |
| 5,304,182 A * | 4/1994 | Rheinish et al. ............. 606/107 |

(List continued on next page.)

FOREIGN PATENT DOCUMENTS

WO          98/37830          9/1998

*Primary Examiner*—Michael H. Thaler
(74) *Attorney, Agent, or Firm*—Fitzpatrick, Cella, Harper & Scinto

(57) ABSTRACT

A device for inserting a flexible membrane into an eye which includes a tubular member with an passage and a plunger movably received in the passage. The passage has an open distal end adapted to be received into an eye for implantation of a lens, and a staging area for initially receiving the lens into the passage. The tubular member includes an opening to permit loading of a lens into the staging area, and a cover movable between an open position to expose the staging area and a closed position to enclose the staging area. The distal end of the plunger has a visual indicator which provides a contrasting image as compared to the staging area. The visual indicator enables the surgeon to easily see whether the distal tip of the plunger is improperly positioned in the staging area before loading the lens.

20 Claims, 8 Drawing Sheets

U.S. PATENT DOCUMENTS

| | | | |
|---|---|---|---|
| 5,395,378 A | 3/1995 | McDonald | |
| 5,425,734 A | 6/1995 | Blake | 606/107 |
| 5,468,246 A | 11/1995 | Blake | 606/107 |
| 5,474,562 A | 12/1995 | Orchowski et al. | |
| 5,494,484 A | 2/1996 | Feingold | |
| 5,496,328 A | 3/1996 | Nakajima et al. | |
| 5,499,987 A | 3/1996 | Feingold | |
| 5,549,614 A | 8/1996 | Tunis | |
| 5,562,676 A | 10/1996 | Brady et al. | |
| 5,578,042 A | 11/1996 | Cumming | |
| 5,582,613 A | 12/1996 | Brady et al. | |
| 5,582,614 A | 12/1996 | Feingold | 606/107 |
| 5,616,148 A | 4/1997 | Eagles et al. | 606/107 |
| 5,620,450 A | 4/1997 | Eagles et al. | 606/107 |
| 5,643,275 A | 7/1997 | Blake | 606/107 |
| 5,643,276 A | 7/1997 | Zaleski | 606/107 |
| 5,653,715 A | 8/1997 | Reich et al. | 606/107 |
| 5,653,753 A | 8/1997 | Brady et al. | 623/6 |
| 5,702,441 A | 12/1997 | Zhou | 623/6 |
| 5,716,364 A | 2/1998 | Makker et al. | 606/107 |
| 5,728,102 A | 3/1998 | Feingold et al. | 606/107 |
| 5,735,858 A | 4/1998 | Makker et al. | 606/107 |
| 5,766,181 A | 6/1998 | Chambers et al. | 606/107 |
| 5,772,666 A * | 6/1998 | Feingold et al. | 606/107 |
| 5,772,667 A | 6/1998 | Blake | 606/107 |
| 5,776,138 A | 7/1998 | Vidal et al. | 606/107 |
| 5,800,442 A | 9/1998 | Wolf et al. | 606/107 |
| 5,803,925 A | 9/1998 | Yang et al. | 606/107 |
| 5,807,244 A * | 9/1998 | Barot | 606/107 X |
| 5,807,400 A | 9/1998 | Chambers et al. | 606/107 |
| 5,810,833 A | 9/1998 | Brady et al. | 606/107 |
| 5,810,834 A | 9/1998 | Heyman | 606/107 |
| 5,860,984 A | 1/1999 | Chambers et al. | 606/107 |
| 5,868,751 A | 2/1999 | Feingold | 606/107 |
| 5,868,752 A | 2/1999 | Makker et al. | 606/107 |
| 5,873,879 A | 2/1999 | Figueroa et al. | 606/107 |
| 5,876,406 A | 3/1999 | Wolf et al. | 604/107 |
| 5,876,440 A | 3/1999 | Feingold | 623/6 |
| 5,944,725 A | 8/1999 | Cicenas et al. | 606/107 |

* cited by examiner

DEVICE FOR INSERTING A FLEXIBLE INTRAOCULAR LENS

BACKGROUND AND SUMMARY OF THE INVENTION

The present invention pertains to a device for inserting a flexible membrane (e.g., a flexible intraocular lens) into an eye of a patient, and in particular, to a device which enhances the surety of properly loading and advancing the membrane.

Intraocular lenses are implanted into eyes to improve a patient's vision. The intraocular lens may be a replacement for a natural crystalline lens or designed to function in conjunction with the natural lens. To minimize the size of the incision in the eye, intraocular lenses are ordinarily formed to be flexible. In this way, the lens can be folded or otherwise compressed to pass through a small incision. The intraocular lens is then permitted to expand to its natural size for proper placement within the eye.

Many devices have been developed for the insertion of a flexible intraocular lens into an eye. These devices typically include a tubular member into which the lens is placed and a plunger for advancing the lens through the passage and into the eye. In a number of these inserters, the lens is first folded into a cartridge which is then loaded into a holder with a plunger for advancing the folded lens into an eye. See, for example, U.S. Pat. No. 5,494,484 to Feingold. These devices, however, require several steps to achieve loading and positioning of the lens for advancement into an eye. In other devices, the tubular member containing the plunger directly receives a generally unstressed lens into a staging area of the central passage via a lateral opening in the device. See, for example, International Patent Application No. PCT/US95/09973 to Figueroa et al. In this device, the lens is folded as it is advanced toward the eye by an internal contour of the passage. Accordingly, this device reduces the number of steps needed to load a lens into an insertion device.

When a generally unfolded lens is placed directly into a tubular member, it is usually important for the plunger to engage the lens in a particular manner to effect proper compressing and advancement of the lens into an eye. The plunger may be specially configured to grasp or engage the lens in a particular way. As an example, the plunger in the noted Figueroa application is provided with a slot which is dimensioned to grasp and hold the lens in order to prevent undesired twisting of the lens and to better control the expansion of a lens inserted into an eye. An improper engagement between the lens and the plunger may result in damage to the lens, a loss of control in folding the lens, or an inability to properly advance the lens.

The components of these non-cartridge insertion devices have in the past been composed of a natural, uncolored clear or translucent plastic material. Consequently, the appearance of the plunger tends to blend into the staging area which may result in the surgeon failing to notice the improper position of the plunger. Accordingly, the plunger has at times been inadvertently advanced too far into the insertion device such that the distal tip of the plunger is improperly positioned in the staging area when the lens is loaded. In this position, the lens is set onto the distal tip of the plunger such that the end of the plunger cannot properly engage the lens.

In the present invention, the distal end of the plunger has a visual indicator which provides a contrasting image as compared to the staging area for supporting the lens. The visual indicator thus enables the surgeon to easily see whether the distal tip of the plunger has encroached into the staging area before loading the lens. The visual indicator may consist of providing the distal end of the plunger with a contrasting color. While cartridge type inserters have been produced with different colored plungers, these devices in no way offer a visual indicator for the surgeon during loading of the lens. Rather, the lens in these inserters is loaded and folded in a cartridge separate and apart from the holder containing the plunger.

DETAILED DESCRIPTION OF THE PREFERRED EMBODIMENTS

The present invention is directed to an improved insertion device which includes a tubular member having a passage for directing a flexible intraocular lens into an eye and a plunger received within the passage for advancing the lens through the passage. In a preferred embodiment, the present invention is incorporated into an insertion device having the construction and operation as disclosed in co-pending U.S. patent application Ser. No. 08/615,185, filed Jun. 25, 1996, which is hereby incorporated in its entirety by reference. Nevertheless, the invention is not limited to this particular construction of an inserter. Rather, the invention has general applicability for inserters wherein the intraocular lens is loaded into the passage of a tubular member which contains a plunger.

Figure 1:
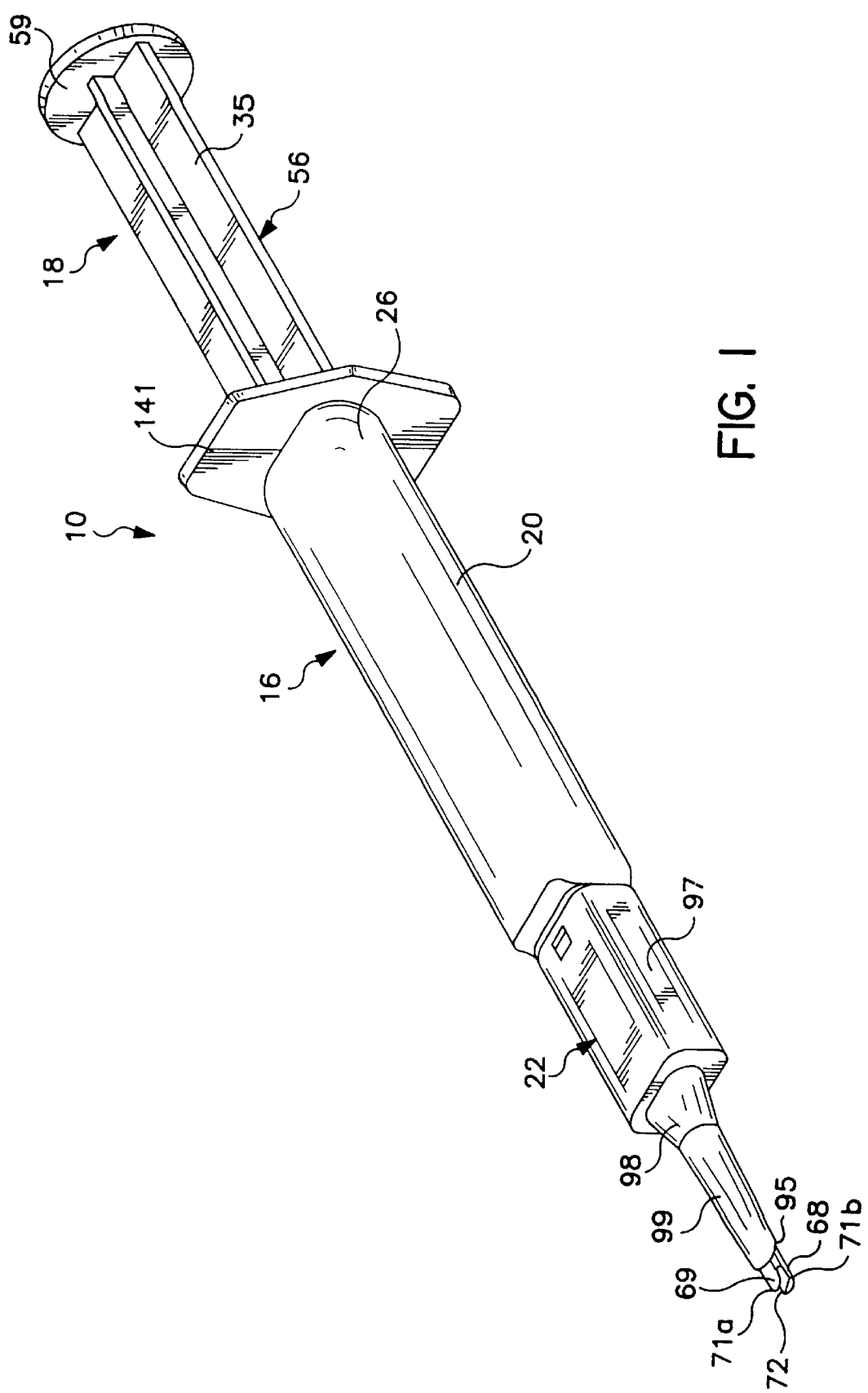
FIG. 1 is a perspective view of a device for inserting an intraocular lens in accordance with the present invention.
Figure 9:
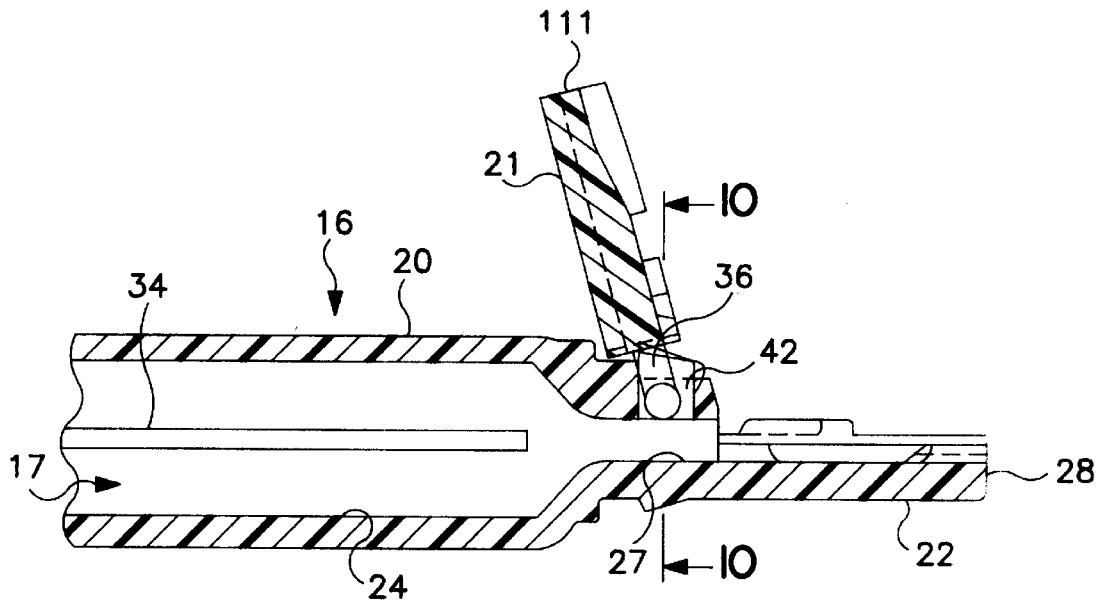
FIG. 9 is a partial cross-sectional view of the tubular unit with the cover open and the cannula omitted.
Figure 10:
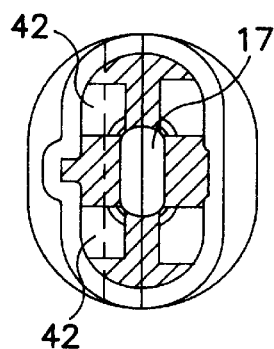
FIG. 10 is a cross-sectional view taken along line 10—10 in FIG. 9, without the cover.
Figure 11:
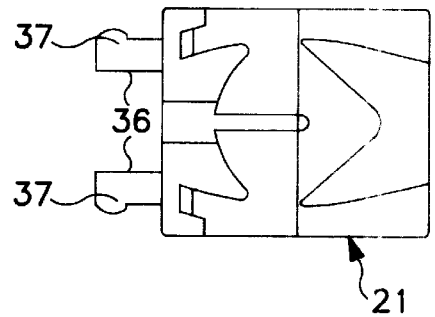
FIG. 11 is a plan view of the inside of the cover.
Figure 15:
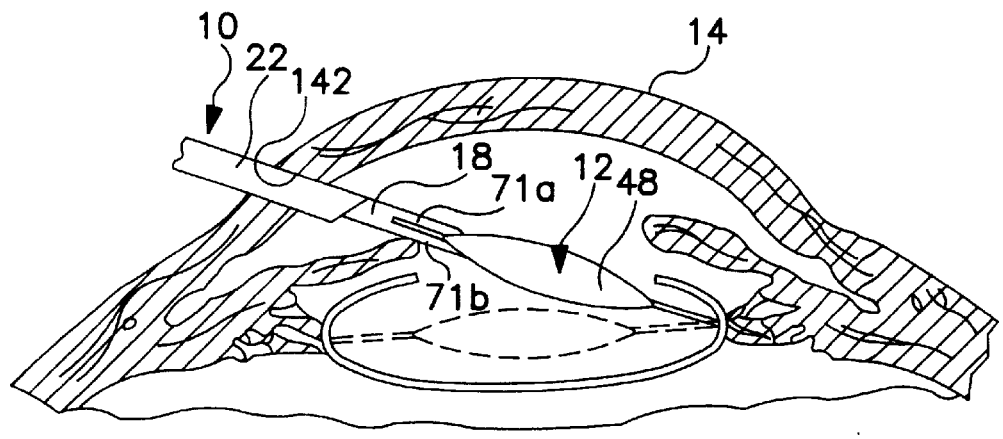
FIG. 15 is a cross-sectional view of an eye illustrating the insertion and placement of an intraocular lens into an eye.

In a preferred embodiment, the present invention includes a device 10 for inserting a flexible membrane, such as a flexible intraocular lens 12, into an eye 14 of a patient (FIGS. 1 and 15). The device comprises a tubular member 16 having a passage 17 and a plunger 18 movably received within the passage. The tubular member preferably includes a base member 20, a cover 21, and a cannula 22 which are coupled together (FIGS. 1 and 9). The components of the device are preferably composed of a plastic material.

Base member 20 is an elongate tubular element defining a passageway 24 which is provided with a relatively large opening at proximal end 26 and an opening 27 of reduced size near, but spaced from, distal end 28 (FIGS. 1, 8, 9 and 12). Passageway 24 of base member 20 is adapted to movably receive and guide plunger 18. A longitudinal groove 34 is preferably positioned along one of the side walls 32 of passageway 24 to receive a flange 35 of the plunger and prevent twisting of the plunger during use.

A forwardly extending deck 29 projects beyond opening 27 to form a staging area 45 for initially receiving the lens. A cover 21 is pivotally attached to base member 20 and is movable between an open position to facilitate loading of a lens onto the deck, and a closed position where the cover overlies the deck and encloses the lens. Cover 21 preferably includes a pair of rearwardly extending arms 36 provided with knobs 37 on their free ends. The free ends of the arms 36 are fit into sockets 42 in base member 20 to form a hinge for the cover. Of course other connections could be used to pivotally attach the cover for movement about either a longitudinal or transverse axis. The internal surfaces of deck 29 and cover 21 are configured to control the folding of the intraocular lens as the lens is advanced toward the eye. The shapes and functions of these surfaces are described in the above-noted U.S. patent application Ser. No. 08/615,185.

Figure 2:
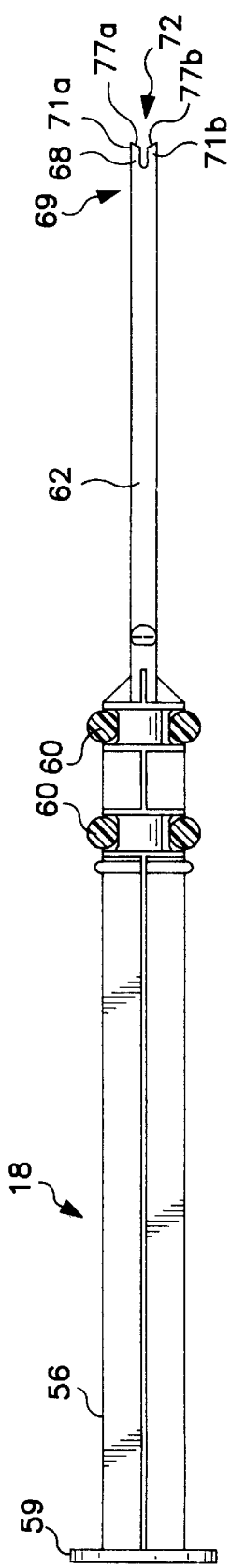
FIG. 2 is a side elevational view of the plunger of the device.
Figure 3:
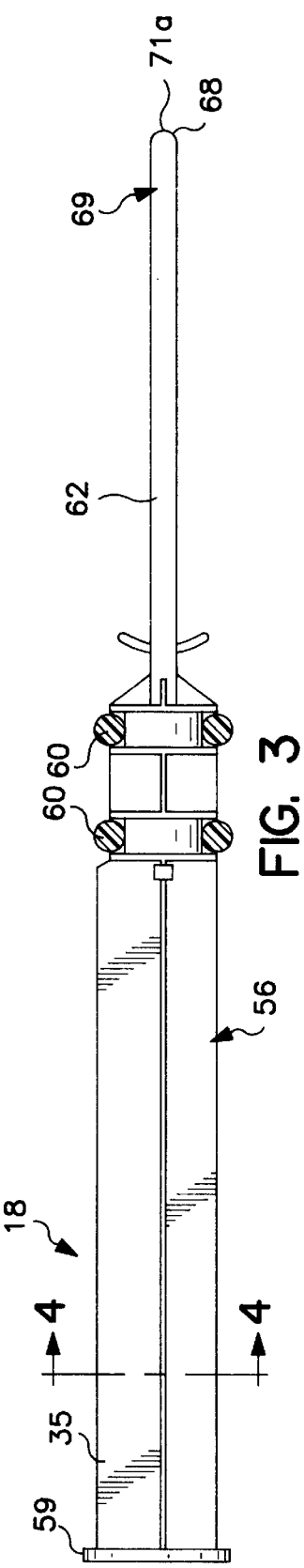
FIG. 3 is a top plan view of the plunger.
Figure 4:
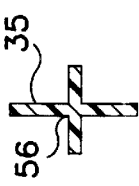
FIG. 4 is a cross-sectional view taken along line 4—4 in FIG. 3.
Figure 5:
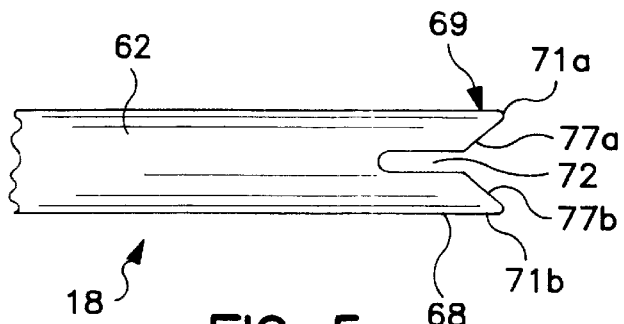
FIG. 5 is a side elevational view of the distal end of the plunger.
Figure 6:
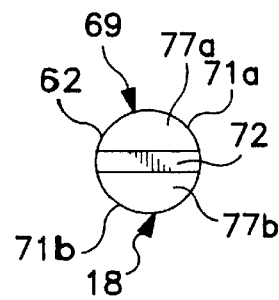
FIG. 6 is a front view of the distal end of the plunger.
Figure 7:
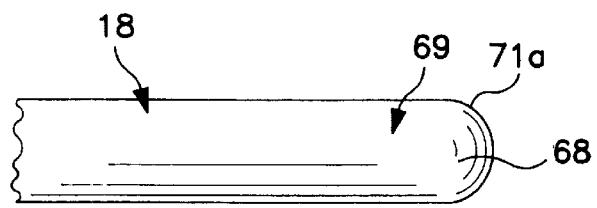
FIG. 7 is a top plan view of the distal end of the plunger.
Figure 8:
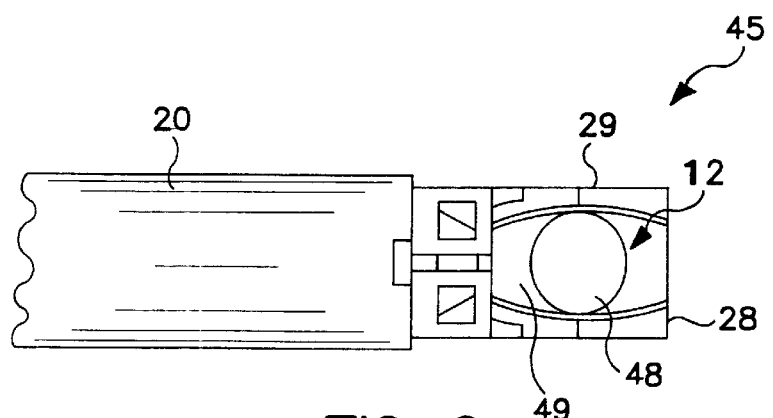
FIG. 8 is a partial top plan view of the tubular unit of the insertion device with an intraocular lens in the staging area and with the cover and cannula omitted.

Plunger 18 is an elongate member which is adapted to move through the passage 17 of tubular member 16 (FIGS. 1–7). The plunger comprises a main body 56 preferably shaped with a cross-shaped cross section, although other constructions could be used. As discussed above, one flange 35 of the body is received into groove 34 (FIGS. 2–4 and 8). A flat thumb pad 59 is provided on the proximal end of body 56 for manual operation of the device (FIGS. 1–3). Other constructions, however, may be provided to effect advancement of plunger 18 through tubular member 16. The forward end of body 56 includes a pair of spaced apart O-rings 60 (FIGS. 2–3). The O-rings provide a level of resistance to enable a more controlled manual operation of the plunger. The O-rings further help to prevent the plunger from inadvertent movement when the surgeon manipulates device 10 during the surgical procedure. Other constructions, such as friction fit flanges, could be used in place of the O-ring. A slender rod 62 projects forwardly beyond the main body 56 of plunger 18 (FIGS. 1–3 and 5–7). The rod engages the lens at the staging area 45 and advances the lens into an eye.

The distal tip 68 of rod 62 is preferably bifurcated to define a pair of prongs 71a, 71b separated by a slot 72 (FIGS. 1–3 and 5–7). The slot is shaped to receive and hold a proximal plate haptic 49 and optic 48 of lens 12. The ends of prongs 71a, 71b are chamfered to form a pair of walls 77a, 77b which collectively form a generally V-shaped configuration. Depending on the sturdiness of the proximal haptic, walls 77a, 77b may or may not engage the proximal end of optic 48. Of course, the distal tip 68 of plunger 18 may alternatively be formed with other structural configurations to engage the disclosed lens as well as other types of lenses (including lenses with loop haptics) when the lens is pushed toward the eye.

In accordance with the present invention, the distal end 68 of plunger 18 is provided with a visual indicator 69 which can be easily seen by the surgeon when extended beyond opening 27 (FIGS. 2–3, 5–7, and 12). The visual indicator is preferably formed by providing the distal end with a color which contrasts with the color of the staging area so as to be easily seen by a surgeon if the end of the plunger is improperly advanced into the staging area. With such an indicator, the surgeon is much less likely to load a lens overtop of the distal end of the plunger. In addition, opening 27 adjacent staging area 45 preferably conforms closely to the size of rod 62 so that the visual indicator is substantially hidden from view when the plunger is properly positioned. While the relationship of opening 27 with rod 62 is not essential, it enables the surgeon to more easily identify when the plunger is improperly positioned. The visual indicator will also help the surgeon see whether the plunger properly engages the lens. For instance, in the present embodiment, the surgeon will be better able to see that the lens is engaged in slot 72 when the plunger is advanced after loading of the lens.

As an example, the visual indicator 69 can be provided by forming the tubular base member 20 with deck 29 with a natural, uncolored clear or translucent appearance (which for purposes of this application is considered a color), and the distal end of the plunger to be dark blue. As a manufacturing expedient, the entire plunger may be formed as a uniform color, but only the distal end acts a visual indicator for the surgeon. Alternatively, the indicator may consist of colored markings or regions on the distal end of the plunger, as opposed to the entire distal end, so long as the markings or regions are plainly and strikingly visible to the surgeon when the cover is open.

Once the lens has been properly loaded, the cannula 22 is fit over the cover 21 and deck 29 (FIG. 1). Cannula 22 is an elongate tubular member with an open proximal end and an opposite open distal end 95. The proximal section 97 of the cannula has a generally rectangular configuration which defines a cavity to matingly receive the assembled deck 29 and cover 21. The medial section 98 of cannula 22 is smaller than proximal section 97 so that a shoulder is placed in abutment with the aligned distal ends 28, 111 of base member 20 and cover 21. The inner wall of medial section 98 converges to define a funnel shaped passageway. This funnel section causes the lens to become substantially curled and compressed for entry into the eye. The distal section 99 of cannula 22 is a long, narrow tube which defines a lumen. Distal section 99 is adapted to be inserted through the narrow incision made in the eye.

Figure 12:
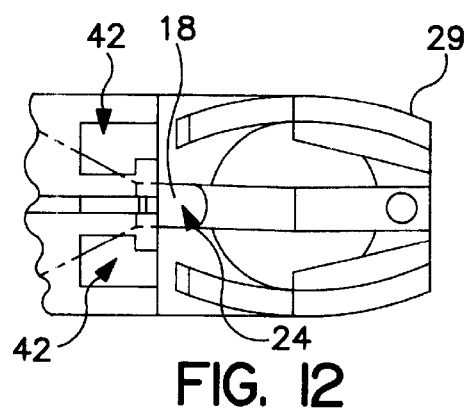
FIG. 12 is a plan view of the inside of the deck of the tubular member.
Figure 13:
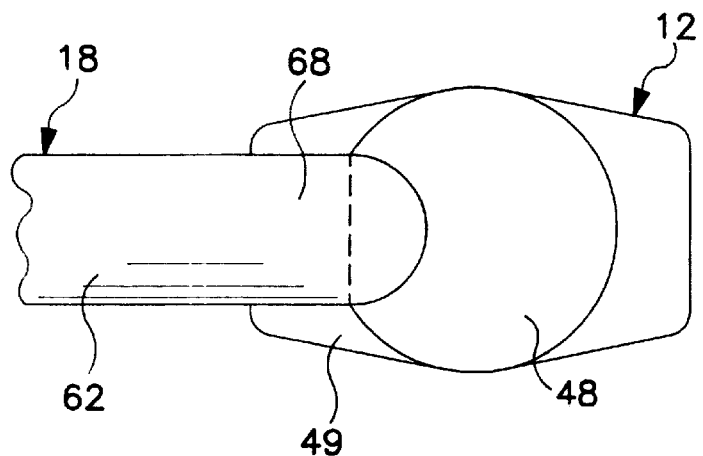
FIG. 13 is an enlarged top plan view of the distal tip of the plunger holding an intraocular lens.
Figure 14:
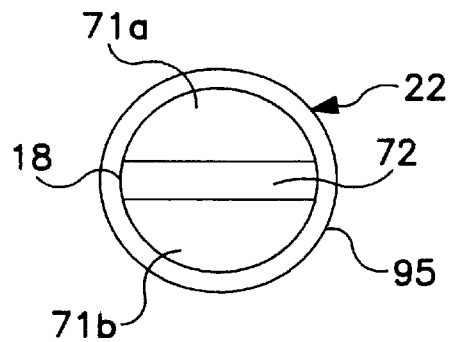
FIG. 14 is a front end view of the device with the plunger extended to the distal end of the cannula.

To load the lens into insertion device 10, the cover 21 is opened to expose the staging area 45 on the upper side of deck 29. With the distal segment of the plunger having a visual indicator which contrasts with the staging area, the surgeon can easily see if the plunger has been advanced beyond opening 27 and into the staging area (FIG. 12). If the plunger is in the staging area, the surgeon retracts the plunger into passageway 24 prior to loading the lens. After the lens has been loaded onto deck 29, the plunger is advanced so that the distal end 68 engages the lens 12. The visual indicator enables the surgeon to better see this engagement and thereby avoid operational problems due to faulty loading. Thereafter, the cover is closed and the cannula fit over the deck and the cover. A viscoelastic material, typically used for such surgical procedures as a lubricant for the insertion process, is placed in the cannula 22 prior to attachment of the cannula 22 to the assembly.

In use, the surgeon inserts the distal end of cannula 22 into the incision 142 in the eye 14 (FIG. 15). The surgeon grasps lateral flanges 141 and pushes on pad 59 to move plunger 18 in a forward motion. The plunger 18 acts to push lens 12 through open end 95 and beyond cannula 22. In the preferred construction, plunger 18 is pushed manually forward in a controlled manner, although other means, such as an electric motor or pneumatic drive, may be used.

Figure 16:
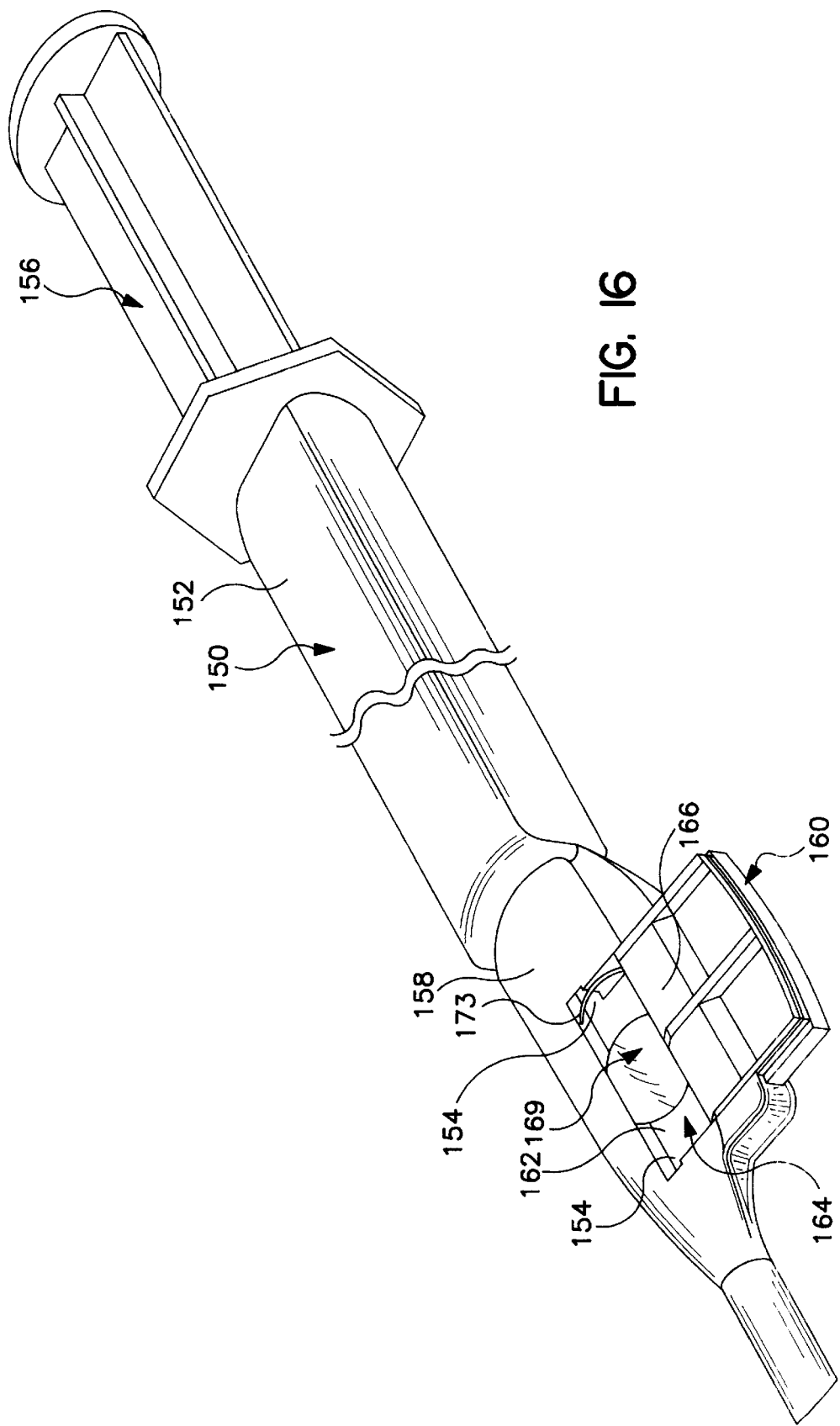
FIG. 16 is a perspective view of an alternative inserter in accordance with the present invention.
Figure 17:
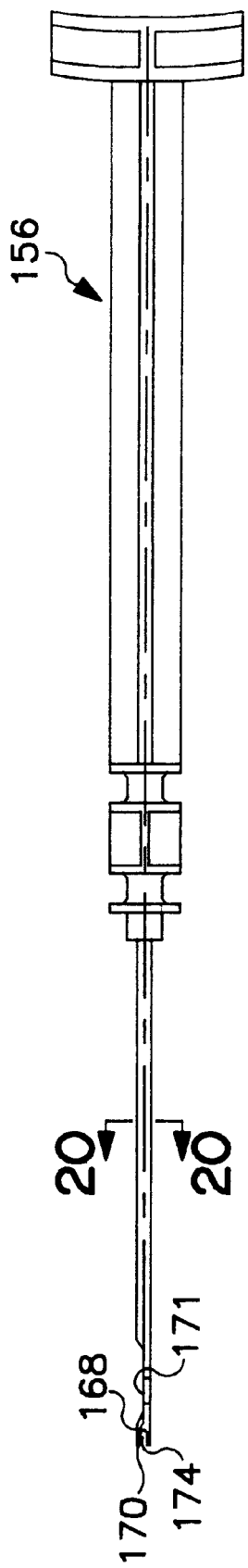
FIG. 17 is a side view of a plunger of the alternative inserter.
Figure 20:
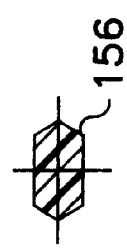
FIG. 20 is a cross-sectional view taken along line 20—20 in FIG. 17.

As another example, a visual indicator as described above can be provided on the distal end of the plunger of U.S. patent application No. 08/721,349, filed Sep. 26, 1996, which is hereby incorporated in its entirety by reference. As seen in FIGS. 16 and 17, device 150 comprises a tubular member 152 having an axial passage 154, and a plunger 156 movably received in the passage. The tubular member 152 is preferably composed of a base member 158 and a movable compressor 160 for compressing the lens. A staging area 162 is provided in passage 154 for initially receiving the lens through an opening 164 defined in the device. A cover 166 is attached to the compressor 160 for movement between an open position to permit placement of the lens in the staging area and a closed position to enclose the passage for use in implanting a lens in an eye. As with device 10, a visual indicator 168 is provided on the distal end of plunger 156 so that the surgeon can more easily see whether the distal tip of the plunger has been properly positioned in the staging area before loading the lens 169, and to more easily see that the plunger has properly engaged the lens after loading of the lens into the staging area.

Figure 19:
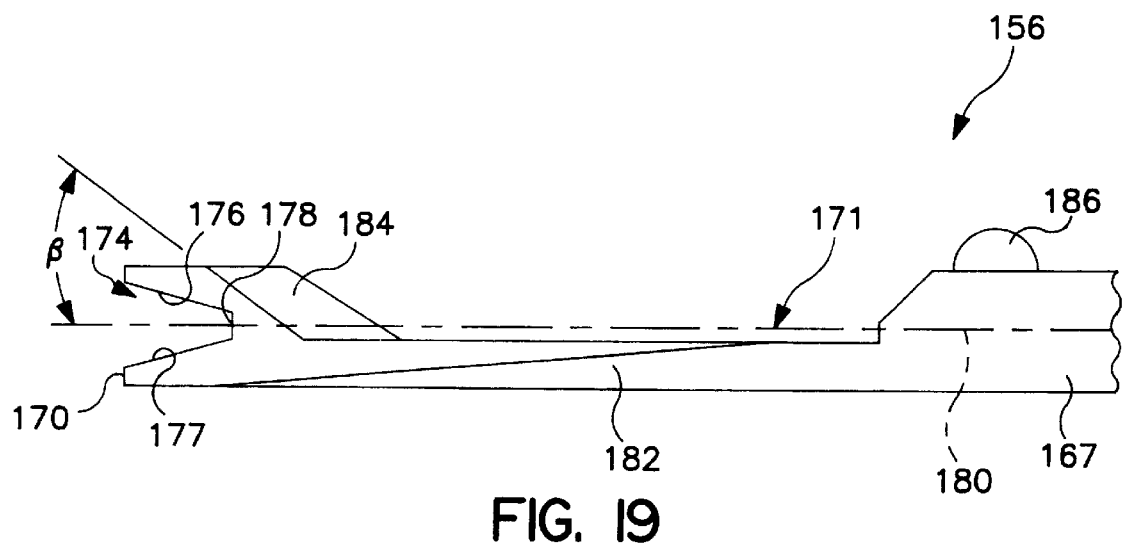
FIG. 19 is an enlarged side view of the distal end of the plunger of the alternative inserter.

In the preferred construction, plunger 156 has an elongate, slender distal end 167 adapted to engage and advance an intraocular lens through the narrow passage 154 and into an eye. The distal end wall 170 of plunger 156 is formed with a concave configuration to engage and hold the proximal edge of the lens optic (FIG. 19). End wall 170 preferably has a forwardly opening, generally V-shaped slot 174 with tapered opposing faces 176, 177 and an inner face 178. Tapered faces 176, 177 are symmetrically positioned about axis 180 of the plunger at about a 30° angle relative to each other to guide the lens into the slot. The tapered faces extend inward about 1 mm (although other depths could be used) to hold the proximal edge of the optic in the slot while the lens is compressed and advanced. The slot construction and dimensions could be much different.

Figure 18:
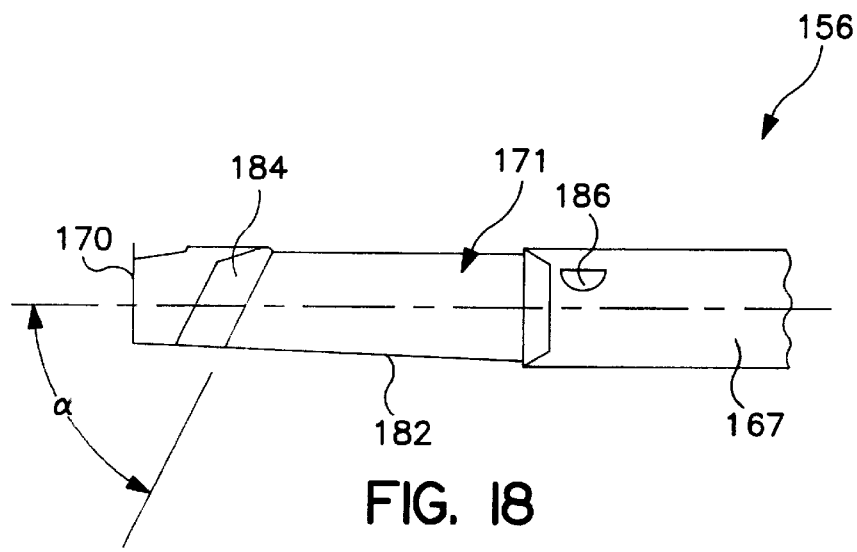
FIG. 18 is an enlarged top view of the distal end of the plunger of the alternative inserter.

The distal end of the plunger further includes a transverse recess 171 for receiving the trailing loop haptic 173 of the lens (FIGS. 18 and 19). The recess 171 protects the trailing haptic from being damaged as the plunger pushes against the optic. One side 182 of the plunger tapers inwardly as it extends toward end wall 170 to provide clearance for haptic 173 extending from the optic. The front wall 184 of recess 171 is inclined toward the end wall 170 as it extends toward side 182 at an angle (e.g., about 60° to axis 180) to minimize the recess and provide sufficient clearance for the haptic when the lens is first loaded into device 150. Front wall 184 is also inclined along the axis at an angle β (e.g., of about 35° to axis 180) to form a ramp and ease the release of the haptic from the recess 171. The ramp-shaped front wall 184 alleviates catching the trailing haptic on the front wall when the lens is released into the eye. The noted angular dimensions are merely examplary and could vary widely.

Plunger 156 also preferably includes a projection or bump 186 along the distal end of the plunger which presses against an internal face of passage 154. The bump eliminates lateral play in the plunger and aids in aligning the slot with the loaded lens. Although many shapes could be used, the bump preferably has an outer arcuate surface to minimize the additional friction caused by the bump.

In use, a surgeon first checks device 150 to ensure that the plunger 156 is properly positioned for loading of the lens into the staging area 162. As discussed above, the visual indicator 168 enables the operator to easily see if the plunger is properly positioned. In this case, the plunger is intended to be positioned slightly into the staging area so that the trailing haptic can be set in recess 171 when loading the lens. However, advancement of the plunger too far into the staging area could result in the optic of the lens being loaded overtop of end wall 170 such that engagement with slot 174 is not effected. In proper operation, the lens is loaded so that the optic is placed forward of end surface 170 and the trailing haptic 173 is set in recess 171. The plunger is then advanced so that the optic is received into the slot 174 in end surface 170. The compressor 160 is pressed inwardly to compress the lens and move cover 166 to its closed position. In this position, the device is ready to move the enclosed lens into an eye.

The above discussion concerns the preferred embodiments of the present invention. Various other embodiments as well as many changes and alterations may be made without departing from the spirit and broader aspects of the invention as described in the claims.

What is claimed is:

1. A device for inserting a flexible membrane into an eye, comprising:
    a tubular member including a passage having an open distal end adapted to be received into the eye and a staging area for initially receiving the flexible membrane into said passage, said tubular member having an opening for loading the flexible membrane into said staging area; and
    a unitary plastic plunger movably received within said passage for advancing the flexible membrane into the eye, said plunger having a distal end adapted to contact the flexible membrane, and said distal end having a visual indicator comprising at least one colored region having a first color different than a second color of a remaining portion of the plunger and that contrasts visibly with a color of said staging area so that said visual indicator is plainly seen when in said staging area,
    wherein, when said visual indicator is plainly seen to be in said staging area prior to loading of the flexible membrane into the staging area, said plunger is retracted to a position where said visual indicator is withdrawn from said staging area.

2. A device in accordance with claim 1 in which the entire distal end of said plunger is formed of the first color.

3. A device in accordance with claim 1 in which said staging area has a natural clear or translucent appearance.

4. A device in accordance with claim 3 in which said distal end of said plunger is blue.

5. A device in accordance with claim 1 in which said distal end of said plunger is blue.

6. A device in accordance with claim 1 in which said distal end of said plunger includes an end face with a concave configuration adapted to engage the flexible membrane.

7. A device in accordance with claim 6 in which said concave configuration includes a slot adapted to engage and hold the flexible membrane.

8. A device in accordance with claim 1 in which said passage includes an axial, narrow opening adjacent said staging area which substantially conceals said visual indicator when said plunger is withdrawn from said staging area.

9. A device in accordance with claim 1 further including a cover attached to said tubular member for movement between an open position to expose said staging area and a closed position to substantially enclose said staging area.

10. A device in accordance with claim 1 in which said passage narrows between said staging area and said open distal end, so as to compress the flexible membrane as it is advanced from said staging area through said open distal end into the eye, wherein said visual indicator is plainly seen in said staging area before the flexible membrane is compressed by said narrowing passage.

11. A device in accordance with claim 10, wherein the flexible membrane is received in said staging area in an uncompressed state, and said distal end is arranged to contact the flexible membrane before the flexible membrane is compressed.

12. A device in accordance with claim 10, wherein said staging area includes a movable member adapted to engage the flexible membrane and at least partly compress the flexible membrane before said distal end contacts the flexible membrane, and wherein the distal end is arranged to contact the flexible membrane in said partly compressed state.

13. A device in accordance with claim 1, wherein in an upstream direction of said passage adjacent said staging area, said tubular membrane substantially obscures said visual indicator.

14. A process for loading a flexible membrane into a device usable to insert the flexible membrane into an eye, comprising:

providing the device including a tubular member having a passage with an open distal end and a staging area, an opening in the tubular member, and a unitary plastic plunger movably received within the passage, the plunger having a distal end provided with a visual indicator comprising at least one colored region which has a first color different from a remaining portion of the plunger and which visibly contrasts with a color of the staging area so that the visual indicator is plainly seen when in the staging area;

examining the staging area for the visual indicator to determine whether the distal end of the plunger extends into the staging area;

retracting the plunger if in said examining step it is determined that the distal end of the plunger extends into the staging area; and loading the flexible membrane through the opening and into the staging area.

15. A process in accordance with claim 14 wherein the provided device includes a cover for the opening, and wherein said process includes opening the cover to examine the staging area and closing the cover to substantially enclose the flexible membrane in the staging area.

16. A process in accordance with claim 15 further comprising the step of advancing the plunger to engage the flexible membrane prior to closing the cover.

17. A process in accordance with claim 14 wherein said examining of the staging area includes determining whether the distal end of the plunger is not in the staging area.

18. A process in accordance with claim 17 wherein the tubular member of the provided device substantially obscures the visual indicator in an upstream direction of the passage adjacent the staging area, and wherein the plunger is moved to position the plunger outside of the staging area before said loading of the flexible membrane through the opening.

19. A process in accordance with claim 14 wherein said loading of the flexible membrane through the opening includes placing of a trailing haptic in a transverse cutout in the plunger.

20. A process in accordance with claim 14 wherein the flexible membrane is a flexible intraocular lens.

* * * * *

UNITED STATES PATENT AND TRADEMARK OFFICE
CERTIFICATE OF CORRECTION

PATENT NO.    : 6,371,960 B2
DATED         : April 16, 2002
INVENTOR(S)   : Thomas M. Heyman et al.

It is certified that error appears in the above-identified patent and that said Letters Patent is hereby corrected as shown below:

Column 5,
Line 51, "angle" should read -- angle $\alpha$ --.

Signed and Sealed this

Fourth Day of February, 2003

JAMES E. ROGAN
*Director of the United States Patent and Trademark Office*